US006544540B2

(12) United States Patent
Van Koppenhagen et al.

(10) Patent No.: US 6,544,540 B2
(45) Date of Patent: Apr. 8, 2003

(54) BASE-TRIGGERED RELEASE MICROCAPSULES

(75) Inventors: Juanita Elena Van Koppenhagen, Vallejo, CA (US); Herbert Benson Scher, Moraga, CA (US); Kuo-Shin Lee, deceased, late of El Cerrito, CA (US), executor Chi Chang Lee; Ian Malcolm Shirley, Binfield (GB); Philip Wade, Runcorn (GB); Richard Follows, Astley (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/363,324

(22) Filed: Jul. 28, 1999

(65) Prior Publication Data

US 2002/0004059 A1 Jan. 10, 2002

Related U.S. Application Data

(60) Provisional application No. 60/109,795, filed on Jul. 29, 1998.

(51) Int. Cl.[7] ............................................. A01N 25/28
(52) U.S. Cl. .................. 424/408; 424/406; 424/417; 424/418; 424/419; 424/497; 424/DIG. 8; 514/521; 514/531; 264/4.3; 264/4.7; 427/213.33; 428/402.21
(58) Field of Search .................. 424/405, 406, 424/408, 419, 497, 418, 489, 493, DIG. 8, DIG. 11; 525/923; 264/4.3, 4.7; 427/213.33; 428/402.21; 514/521, 531, 532

(56) References Cited

U.S. PATENT DOCUMENTS 3,959,464 A * 5/1976 DeSavigny ................. 424/406
4,508,807 A    4/1985 Adair ......................... 430/138
4,584,334 A    4/1986 Lee, Jr. et al. ............... 524/151
4,956,129 A * 9/1990 Scher et al. ................. 264/4.7
5,160,529 A   11/1992 Scher et al. .................. 71/118
5,332,584 A    7/1994 Scher et al. ................. 424/408
5,750,126 A    5/1998 Smith et al. ................. 424/405
6,022,501 A * 2/2000 Dexter et al. ................ 264/4.7
6,077,522 A * 6/2000 Scher et al. ................. 424/408

FOREIGN PATENT DOCUMENTS

| EP | 0 169 621 | 1/1986 |
| EP | 0 823 993 A2 | 2/1998 |
| GB | 2 280 164 A | 1/1995 |
| WO | 93/14865 | 8/1993 |

* cited by examiner

*Primary Examiner*—Neil S. Levy
(74) *Attorney, Agent, or Firm*—Townsend and Townsend and Crew LLP

(57) ABSTRACT

Microcapsules formed from an aminoplast shell wall and an encapsulated ingredient or ingredients enclosed within the wall in which the wall contains a base-cleavable ester moiety.

These capsules have been found to be sensitive to the presence of base such that in the presence of base, the capsule walls are relatively quickly disintegrated or degraded so as to produce a relatively quick release of the encapsulated materials.

Microcapsules of this invention are particularly suitable for use in controlling insects having an alkaline gut such as certain lepidoptera in that the capsule shell wall may be designed so as to quickly disintegrate under the alkaline conditions present in the gut of the insect thus providing a microcapsule which is safe to handle but which is selectively effective against certain undesirable insects while not harmful to beneficial insects or insects which do not feed on the capsule materials.

36 Claims, No Drawings

BASE-TRIGGERED RELEASE MICROCAPSULES

This invention pertains to certain microencapsulated compositions which contain an active ingredient encapsulated within a polymeric shell wall, particularly an aminoplast shell wall, in which the shell wall contains an ester containing a cross-linking unit, as well as processes for the production of such microcapsules, and methods for their use. The base-sensitive cross-linking unit triggers release of the encapsulated contents on exposure of the capsules to basic conditions.

The microcapsules of this invention have been found particularly suitable for use in producing encapsulated formulations of pesticides, for both agricultural and non-agricultural use. They are also suitable for encapsulated formulation of non-pesticidal agricultural chemicals such as plant growth regulators, insect growth regulators, fertilizers, and other agriculturally useful materials. In addition, they are useful for encapsulation of materials outside the agricultural field such as detergent powders.

In many instances, particularly in agriculture, the object of producing microencapsulated compositions has been to provide controlled release of the encapsulated active ingredient, and particularly to provide a release for longer term efficacy so that the active ingredient is released over a period of time and is available throughout the effective period. This is particularly significant for pesticides or other ingredients which are degraded or decomposed over a relatively short period of time under certain environmental conditions. Use of microencapsulated compositions in these situations provides effective activity of the encapsulated ingredient over a longer period of time since it will be released continuously into the environment in the amount needed rather than in one large initial dose.

Currently, microencapsulated pesticides are used primarily as preemergence pesticides, that is, they are applied to soil prior to the emergence of vegetation or the appearance of insects, so that they are available to kill or control newly emerged weed species or insects in their larval stages. Again, in those applications, relatively slow release rates are desired so that the pesticide is released into the environment over a period of time, usually over at least several weeks.

Microencapsulated formulations for quick release are known in a number of other applications, such as the printing and xerography industries, in which materials such as inks, pigments, toner particles, etc., are microencapsulated and released quickly upon application of physical force or heat. Microcapsules with comparatively quick release could have utility in agriculture in situations in which controlled release is not desired, but microencapsulation of the active ingredient is desired for any of a number of reasons. For example, microencapsulation can be desired to protect against dermal effects of pesticides during their handling (for instance, production, storage or loading into spray equipment). However, a comparatively quick release of the pesticide may be desired in order to make the pesticide readily available to control a pest, as is usually the case with nonencapsulated or non-controlled release formulations such as solutions, emulsions, dusts, powders, granules, etc. Another instance in which it is desirable to have encapsulation but comparatively quick release of a pesticide is in the production of pesticidal products containing two active ingredients which may be reactive with each other or otherwise incompatible in a single system.

Microencapsulation of pesticides may often provide an increase in the safety of pesticide handling, to the extent that the polymer wall of a microcapsule minimizes contact of the handler with the active pesticide, particularly if the pesticide is in the form of a suspension of microcapsules. The provision of a comparatively quick release microencapsulated formulation of a pesticide could minimize contact of a handler with the active pesticide, yet provide the necessary release of the active ingredient when applied to protect plants from an insect pest which is already present or about to invade. Additionally, such encapsulated products containing pyrethroids could be useful in industrial, commercial or residential pest control.

SUMMARY OF THE INVENTION

This invention provides microcapsules which satisfy the above-mentioned objectives.

In one aspect, this invention comprises a microcapsule formed of an aminoplast shell wall and an encapsulated ingredient or ingredients enclosed within the wall, the wall produced by a microencapsulation process comprising reacting an amino resin prepolymer with a compound having one or more ester or thioester groups which are cleaved under basic conditions and two or more other functional groups capable of reacting with the resin.

Preferably this compound is a cross-linking agent produced by reaction of a multifunctional $C_1$–$C_{20}$ aliphatic or cycloaliphatic alcohol containing at least two, preferably at least 3, functional groups which are capable of esterification, such as pentaerythritol, dipentaerythritol, tripentaerythritol, trimethylolpropane, glycerol, mercaptoethanol, 3-mercaptopropane-diol, 1,2,4-butanetriol, 1,3,5-cyclohexanetriol, 1,2,3-heptanetriol, sorbitol, or 2,3-dimercapto-1-propanol with one or more 2-(hydroxy or thiol) substituted $C_2$–$C_6$ alkanoic acids.

In another aspect, this invention comprises a process for the production of such microcapsules comprising reacting an amino resin prepolymer with a compound having one or more ester or thioester groups which are cleaved under basic conditions and two or more other functional groups capable of reacting with the resin.

Preferably this compound is a cross-linking agent produced by reaction of a multifunctional $C_1$–$C_{20}$ aliphatic or cycloaliphatic alcohol containing at least two, preferably at least 3, functional groups which are capable of esterification, such as pentaerythritol, dipentaerythritol, tripentaerythritol, trimethylolpropane, glycerol, mercaptoethanol, 3-mercaptopropane-diol, 1,2,4-butanetriol, 1,3,5-cyclohexanetriol, 1,2,3-heptanetriol, sorbitol, or 2,3-dimercapto-1-propanol with a 2-(hydroxy or thiol) substituted $C_2$–$C_6$ alkanoic acid.

DETAILED DESCRIPTION OF THE INVENTION

This invention relates to microcapsules containing an encapsulated substance which are cleaved in the presence of base; and can be designed so as to break down or disintegrate relatively quickly under basic conditions so as to release the encapsulated substance into the surrounding environment.

The microcapsules are characterized by having an aminoplast shell wall produced by a microencapsulation process comprising reacting an amino resin prepolymer with a compound having one or more ester or thioester groups which are cleaved under basic conditions and two or more other functional groups capable of reacting with the resin. Preferably the amino resin is an etherified resin.

Preferably this compound is a cross-linking agent produced by reaction of a multifunctional $C_1$–$C_{20}$ aliphatic or cycloaliphatic alcohol containing at least two, preferably at least 3, functional groups which are capable of esterification, such as pentaerythritol, dipentaerythritol, tripentaerythritol, trimethylolpropane, glycerol, mercaptoethanol, 3-mercaptopropane-diol, 1,2,4-butanetriol, 1,3,5-cyclohexanetriol, 1,2,3-hepanetriol, sorbitol, or 2,3-dimercapto-1-propanol with one or more 2-hydroxy $C_2$–$C_6$ alkanoic acids and/or 2-thiol $C_2$–$C_6$ alkanoic acids. If the capsules are not in a basic environment, they function as typical diffusion controlled release microcapsules, permitting release of the encapsulated substance into the surrounding area in a controlled manner which is determined primarily by wall characteristics of the shells such as thickness, capsule size, permeability, etc. If, on the other hand, the capsules are placed in a basic environment, preferably in a situation in which the resulting pH is from about 8 to about 13, preferably from about 9 to about 11, the cross-linking moieties in the capsule wall are cleaved so as to "trigger" or initiate breakdown of the capsule wall. Depending on the conditions of the environment and on the particular structure of the capsule wall, the resulting breakdown may occur relatively quickly or relatively slowly. Comparatively quick breakdown enables comparatively quick (as opposed to controlled) release of the encapsulated substance into the surrounding environment. Capsule walls may be designed so as to produce comparatively quick or comparatively slow breakdown, for instance, by selection of the cross-linking agent and/or the amount used with relation to the amount of wall-forming resin.

The encapsulated material may be any type of material for which capsules of this type are suitable. Preferably the encapsulated material is comprised of a liquid; that is, it may be in the form of a liquid itself, or in the form of a solid which is suspended or dissolved in a liquid, or a mixture of liquids which are dissolved one in the other, or even a liquid emulsion. For purposes of this invention, the products will be described in terms of encapsulation of agricultural or non-agricultural pesticides. However, the invention is not so limited and, as mentioned above, may be used for encapsulation of many suitable materials for many purposes.

When the encapsulated material is a pesticide, again, it may be a single liquid pesticide, a solid pesticide dissolved or suspended in a liquid (in which case the liquid may be an inert material or may be a second pesticide which is in liquid form), or a mixture of liquids dissolved one in the other, or an emulsion. The encapsulated material may also contain other substances such as surfactants, dispersants and the like. If any of the materials, particularly the pesticide, is sensitive to ultraviolet light, the encapsulated liquid material may also contain a protectant, for example, a suspended solid ultraviolet light protectant such as titanium and/or zinc oxide as described in PCT application WO/RIA37824A. As used herein, "pesticides" is meant to include not only typical pesticides such as insecticides, herbicides, fungicides, acaricides, miticides, rodenticides and other materials which are toxic or poisonous to pests, but also chemicals having biological activity on pests such as plant and/or insect growth regulators.

The cross-linking agents have the general formula

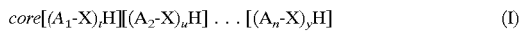

where "core" represents a structure derived from a multifunctional alcohol having at least two, and preferably at least three, functional groups capable of esterification (such as pentaerythritol, trimethylolpropane, glycerol, etc.); $A_1$-X—, $A_2$-X—, ... $A_n$-X— each constitute one or more randomly oligomerized esters of 2-hydroxy $C_2$–$C_6$ alkanoic acids and/or 2-thiol $C_2$–$C_6$ alkanoic acids, where XH represents the terminal alcohol or sulfhydryl capable of reacting with an amino-formaldehyde prepolymer; and n is the number of functional groups on the core capable of reacting with derivatives of the 2-hydroxy and/or 2-thiol $C_2$–$C_6$ alkanoic acids.

Random oligomerization within groups $(A_1\text{-}X)_t$—H, etc. occurs when a mixture of two or more such acids is reacted with the alcohol.

Preferred cross-linking agents are prepared from pentaerythritol or dipentaerythritol. When pentaerythritol is the reactant they have the general formula

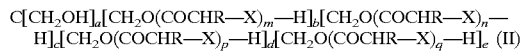

where R is —H or $C_1$–$C_4$ alkyl groups which may alternate randomly; X is oxygen or sulfur which may alternate randomly; $a \leq 2$; and b, c, d, e are zero or a number from 1 to 4, where a+b+c+d+e=4; and m, n, p, and q are independent values from 1 to 20.

The above formula can also be depicted as

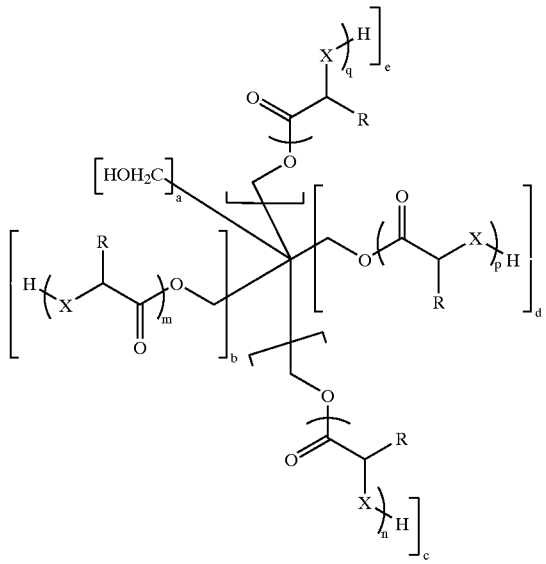

When dipentaerythritol is the reactant the cross-linking agents have the formula

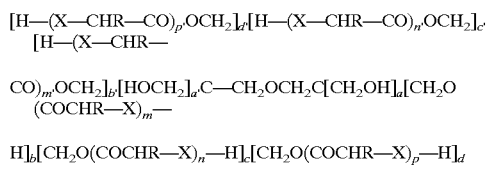

where R is —H or $C_1$–$C_4$ alkyl groups which may alternate randomly; X is oxygen or sulfur which may alternate; a, a'$\leq$2; and b, b', c, c', d, and d' are zero or a number from 1 to 3 where a+b+c+d+a'+b'+c'+d'=6; and m, m', n, n', p, p' are independent values from 1 to 20.

The cross-linking agents are esters which have one or more ester and/or thioester groups which are cleaved under basic environmental conditions as described below.

The ester-containing cross-linking agents of this invention may be prepared by known methods involving the condensation of carboxylic acids or carboxylic acid derivatives with alcohols such as pentaerythritol. To illustrate:

—COZ+HO—→CO—O—+HZ.

Typically Z may be a hydroxyl or methoxyl group when respectively water (Z=—OH) or methanol (Z=—OCH$_3$) would be eliminated. Yields are increased by removing the water or derivative moiety HZ as it is formed in the condensation reaction by such methods as azeotropic distillation, or by heating the mixture above the boiling point of HZ.

Suitable carboxylic acids include thioglycolic acid and glycolic acid. Suitable carboxylic acid derivatives include methyl 2-mercapto-acetate, and methyl glycolate may also be used. These compounds contain alcohol or thiol groups which are capable of reacting with the resin to form microcapsules. However it will be apparent to those skilled in the art that under their preparation conditions the alcohol or thiol groups may take part in self-condensation polymerization reactions with the carboxyl groups to form chains containing ester and thioester linkages:

—COZ+HS—→—CO—S—+HZ

For example, reaction of pentaerythritol with thioglycolic acid and glycolic acid in the presence of a catalyst such as para-toluenesulfonic acid will produce a four-armed star structure illustrated by the formula:

$$C[CH_2OH]_a[CH_2O(COCH_2X)_m—H]_b[CH_2O(COCH_2X)_n—H]_c$$
$$[CH_2O(COCH_2X)_p—H]_d[CH_2O(COCH_2X)_q—H]_e$$

where X is O or S and may alternate randomly; a+b+c+d+e=4; and m, n, p, and q are independent values from 1 to 20. The length and composition of each arm may be variable and will reflect the process conditions and the mole ratios of the three reactants used in the preparation.

The sensitivity of thiols to oxidative coupling requires that reactions at elevated temperatures are kept air free, for example under a vacuum or under a nitrogen blanket.

In one process for the preparation of ester or thioester containing materials of this invention a mixture of pentaerythritol, thioglycolic acid and glycolic acid in toluene or xylene is azeotroped in the presence of a catalyst such as para-toluenesulfonic acid to remove the calculated quantity of water for the desired conversion.

In another process for the preparation of ester or thioester containing materials of this invention a mixture of pentaerythritol, thioglycolic acid and glycolic acid is heated under reflux at about 160° C. in the presence of a catalyst such as para-toluenesulfonic acid. After a given time the reaction vessel is cooled to about 100° C. and the reflux head is reconfigured for distillation to remove water. The choice of the distillation conditions must reflect a balance between (i) the possible loss of reagent such as thioglycolic acid, (ii) the stability of the product at the operating temperature and (iii) the potential for oxidative formation of disulfides on exposure to air.

It will be appreciated that the solubility in water or in organic solvents of pentaerythritol derivatives of the type mentioned above will depend upon the exact composition and on the chain lengths of the 'arm', i.e., on the values of m, n, p and q. For example structures which contain no thioglycolate (i.e., n and p=0) and are of low Mw (e.g. m+q<4) tend to be very soluble in water.

The crude reaction products may be fractionated as a function of their differential solubility in solvents such as ether, chloroform, toluene and water. In addition to fractionation, washing with water may be desirable to remove acid catalysts and any non-reacted reagents. Such purification is preferred if the ester containing materials are to be stored for extended periods before use in microcapsule preparations.

Preferred derivatives for use in this invention may be described by the compositions of the feedstocks or reactants employed in their preparations. Preferred derivatives of pentaerythritol include pentaerythritol diglycolate dimercaptoacetate (PDGDM), tetrathioglycolate (PTT), and monoglycolate trimercaptoacetate (PMGTM) and dipentaerythritol hexathiolactate (DPTA), octamercaptoacetate (DPMA) and diglycolate tetramercaptoacetate (DPDGTM). These are prepared from the following reactants:

| | Mole Ratios in Feedstock | | |
|---|---|---|---|
| Cross-Linker | Pentaerythritol | Glycolic Acid | Mercaptoacetic Acid |
| PDGDM | 1 | 2 | 2 |
| PTT | 1 | 0 | 4 |
| PMGTM | 1 | 1 | 3 |

| | Mole Ratios in Feedstock | | |
|---|---|---|---|
| Cross-Linker | Dipentaerythritol | Thiolactic Acid | Glycolic Acid | Mercaptoacetic Acid |
| DPTA | 1 | 6 | 0 | 0 |
| DPMA | 1 | 0 | 0 | 8 |
| DPDGTM | 1 | 0 | 2 | 4 |

Preferred compositions for use in this invention are prepared from pentaerythritol, thioglycolic acid and glycolic acid in mole ratios of 1:2:2 (PDGDM), 1:4:0 (PTT), 1:3:1 (PMGTM) and from di-pentaerythritol and 2-thioglycolic acid in a mole ratio of 1:6 (DPTA).

Pentaerythritol derivatives such as pentaerythritol tetrakis (mercaptopropionate) (sold under the trademark Mercaptate Q-43 Ester) are known to be useful as wall modifying agents for urea-formaldehyde microcapsules, as disclosed, for instance, in U.S. Pat. Nos. 4,956,129, 5,160,529 and 5,232,584. By reacting with ether or methylol groups in the prepolymer, these derivatives increase the degree of cross-linking, strengthening the wall at this time and decreasing its permeability. While not wishing to be bound by theory, we believe that the cross-linking agents of this invention have relatively weak links in the ester and/or thioester groups (—XCO—; where X=O or S) which are alpha to electron-withdrawing oxygen or sulfur atoms which cause the weak links to be susceptible to hydolysis in the presence of base.

The first step in the reaction between the cross-linker and an etherified amino formaldehyde prepolymer can be represented as:

core(A$_1$—X)$_t$H(A$_2$—X)$_u$H ... (A$_{\overline{n}}$—X)$_y$H +
    cross-linking agent
    B >NCH$_2$OR$_1$    ⟶
    functional group on an etherified amino
    formaldehyde prepolymer*
core(A$_1$—X)$_t$CH$_2$N<][(A$_2$—X)$_u$CH$_2$N<] ... [(A$_{\overline{n}}$—X)$_y$CH$_2$N<] + B R$_1$OH
    aminoplast microcapsule wall

*These functional groups are likely to be on different prepolymer molecules.

where R$_1$=H, or C$_1$–C$_4$ alkyl; "core" is derived from a multifunctional alcohol having at least two, preferably at least three, functional groups capable of esterification (such as pentaerythritol, trimethylpropane, glycerol, etc.); $A_1\text{-}X\text{---}, A_2\text{-}X\text{---}, \ldots A_n\text{-}X\text{---}$ each constitute one or more randomly oligomerized esters of 2-hydroxy $C_2\text{-}C_6$ alkanoic acids and/or 2-thiol $C_2\text{-}C_6$ alkanoic acids, where XH represents the terminal alcohol or sulfhydryl capable of reacting with an etherified amino formaldehyde prepolymer; n is the number of functional groups on the core capable of reacting with derivatives of the 2-hydroxy and/or 2-thiol $C_2\text{-}C_6$ alkanoic acids; and $2 \leq B$.

The symbols $>NCH_2O\text{---}$ and $\text{---}CH_2N<$ are used to indicate the aminoplast resin.

The cross-linking agents are utilized as one of the materials in the production of aminoplast, preferably urea-formaldehyde, microcapsules such that the walls of the resulting capsules contain the cross-linking agents. The capsule walls in combination with the cross-linking ester moieties have the general formula

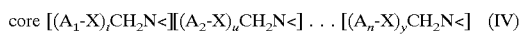

core $[(A_1\text{-}X)_t CH_2N<][(A_2\text{-}X)_u CH_2N<] \ldots [(A_n\text{-}X)_y CH_2N<]$ (IV)

where "core", $A_n\text{-}X\text{---}$ and $\text{---}CH_2N<$ are as defined above.

In general the capsule wall will contain units variously having the formulas $A_1$, (etc.)$SCH_2N<$, $A_1$(etc.)$OCH_2N<$, and $A_1$(etc.)$<N$, the last-mentioned resulting from loss of formaldehyde from a group of the second type.

When pentherythritol is used as a reactant the moiety as present in the wall structure has the general formula

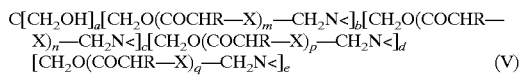

$C[CH_2OH]_a[CH_2O(COCHR\text{---}X)_m\text{---}CH_2N<]_b[CH_2O(COCHR\text{---}X)_n\text{---}CH_2N<]_c[CH_2O(COCHR\text{---}X)_p\text{---}CH_2N<]_d$
$[CH_2O(COCHR\text{---}X)_q\text{---}CH_2N<]_e$ (V)

where R is $\text{---}H$ or $C_1\text{-}C_4$ alkyl groups which may alternate randomly; X is oxygen or sulfur which may alternate randomly; $a \leq 2$; and b, c, d, e are zero or a number from 1 to 4, where $a+b+c+d+e=4$; $2 \leq B \leq b+c+d+e$; and m, n, p, and q are independent values from 1 to 20.

When dipentaerythritol is used as a reactant the moiety as present in the wall structure has the general formula

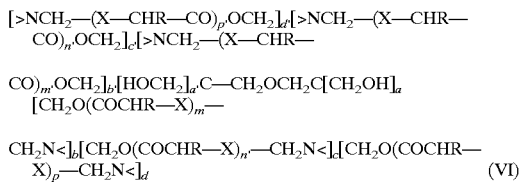

$[>NCH_2\text{---}(X\text{---}CHR\text{---}CO)_p\text{.}OCH_2]_{b'}[>NCH_2\text{---}(X\text{---}CHR\text{---}CO)_{n'}OCH_2]_{c'}[>NCH_2\text{---}(X\text{---}CHR\text{---}$ $CO)_{m'}OCH_2]_{b'}[HOCH_2]_{a'}C\text{---}CH_2OCH_2C[CH_2OH]_a$
$[CH_2O(COCHR\text{---}X)_m\text{---}$ $CH_2N<]_b[CH_2O(COCHR\text{---}X)_n\text{---}CH_2N<]_c[CH_2O(COCHR\text{---}X)_p\text{---}CH_2N<]_d$ (VI)

where R is $\text{---}H$ or $C_1\text{-}C_4$ alkyl groups which may alternate randomly; X is oxygen or sulfur which may alternate randomly; a, $a' \leq 2$; and b, b', c, c', d, and d' are zero or a number from 1 to 3 where $a+b+c+d+a'+b'+c'+d'=6$; $2 \leq B \leq b+b'+c+c'+d+d'$; and m, m', n, n', p, and p' are independent values from 1 to 20.

In general, ingredients for the products of this invention are chosen among those possible so as to exclude combinations which are reactive toward each other. Thus, the choice of the particular pentaerythritol derivative, prepolymer, material to be encapsulated, and other materials is made so as to minimize or prevent undesirable reactions.

The choice of cross-linking agents for use in this invention involves several considerations. For use in the microencapsulation process, the cross-linking agent must be compatible with the oil phase of the emulsion or dispersion which is utilized, as will be discussed below, to produce the microcapsules. In addition, the cross-linking agent must be able to survive the conditions of microcapsule wall formation (acidic conditions and preferred temperatures of approximately 20–80° C. as well as long-term storage at such temperatures and pH values of about 5.5 to about 7.5. As will be discussed below, when a comparatively quick release is desired, for instance quick release of the encapsulated contents in the gut of an insect, to be effective in triggering such release the cross-linking agent also must be rapidly hydrolyzed by a pH swing from ±5.5±to ±9±.

The process for producing aminoplast or urea-formaldehyde microcapsules is described in U.S. Pat. Nos. 4,596,129 and 5,160,529, which are hereby incorporated herein, and is generally as follows:

An organic solution or oil phase is provided which comprises the material to be encapsulated, an etherified amino resin prepolymer, preferably dissolved in the material to be encapsulated, and in which from about 50% to about 98% of the methylol groups of the prepolymer have been etherified with a $C_4\text{-}C_{10}$ alcohol, and the cross-linking agent, the latter preferably dissolved in the material to be encapsulated. Then, an emulsion of this organic solution or oil phase is created in a continuous phase aqueous solution comprising water and a surface-active agent, in which the emulsion comprises discrete droplets of the organic phase dispersed in the aqueous phase, such that there is formed an interface between the discrete droplets of the organic phase and the surrounding continuous phase aqueous material. Then, in situ condensation between the resin and cross-linker, and curing of the resulting polymer in the organic phase adjacent to the interface between the phases is produced by simultaneously heating the emulsion to a temperature of from about 20° C. to about 100° C. and adding to the emulsion an acidifying agent, and maintaining the emulsion at a pH of between about 0 and about 4 and a temperature of from about 20 to about 60° C. for a sufficient period of time to allow substantial completion of in situ condensation of the resin prepolymer and cross-linker so as to convert the liquid droplets of the organic phase to capsules which consist of solid permeable polymer shells enclosing the encapsulated liquid material.

The organic phase or solution must be substantially insoluble in water. Preferably its solubility under ambient conditions is approximately 5,000 ppm by weight or less. The organic solution may consist of a single liquid material or one or more liquid active or solid materials dissolved in an inert solvent which at most has a slight solubility to water, or may consist of a suspension of solid materials in such an organic liquid.

A wide variety of liquids can be encapsulated by this process, and include chemical-biological agents including both pesticides and non-pesticidal materials suitable for use in agriculture and in pest control. These include herbicides, insecticides, fungicides, nematicides, bactericides, rodenticides, moluscicides, acaricides, larvaecides, pesticidal viruses and proteins, animal, insect and bird repellents, plant and insect growth regulators, fertilizers, pheromones, sex lures and attractants, and flavor and odor compositions. Included with the pesticide may be materials typically used in conjunction with it such as synergists and/or safeners.

One particularly useful type of pesticide in this invention is insecticides, particularly those known to be effective as stomach poisons. As will be discussed below, quick release microcapsules of this invention may be particularly useful for control of insects which have predominantly alkaline conditions in the gut.

The prepolymers useful in the present invention are those known from the above-mentioned U.S. patents; namely, partially etherified amino resin prepolymers with a high solubility in the organic phase and a low solubility in water.

In the non-etherified form, the prepolymer contains a large number of methylol groups in its molecular structure. Etherified prepolymers have the hydroxyl hydrogen atoms replaced by alkyl groups and are obtained by condensation of a compound containing amino groups with formaldehyde and an alcohol. The prepolymers are soluble in the organic phase when the alkyl groups have four or more carbon atoms and in which more than about 50% of the hydroxyl hydrogen atoms on the prepolymer molecule have been replaced. Those useful in the above process are those in which from about 50% to about 98% of the hydroxyl hydrogen atoms have been replaced by alkyl groups, as some hydroxyl groups are needed for the condensation/polymerization which occurs in the wall forming step. Preferably from about 70% to about 90% of the methylol groups have been etherified with preferably a $C_4$–$C_6$ alcohol. The alcohol may be straight or branched chain.

The amino resin may be one of four general types: urea-formaldehyde, melamine-formaldehyde, benzoguanamine-formaldehyde and glycoluril-formaldehyde. The first two mentioned are preferred, with urea-formaldehyde prepolymers being most preferred. The prepolymers utilized may be commercially available etherified amino resin prepolymers. Some commercially available etherified prepolymers are those sold by Cytec under the trademarks Beetle® and Cymel®, the Beckamine® line sold by Reichhold Chemicals, and the Resimen® line sold by Solutia.

The prepolymers can also be prepared by known techniques, for instance, by the reaction between the amine (preferably urea or melamine), formaldehyde and alcohol. The organic solution may also contain optional additives such as solvents and polymerization catalysts.

The amount of the prepolymer in the organic phase is not critical to the practice of this invention, but can vary over a wide range depending on the desired capsule wall strength and the desired quantity of core liquid in the finished capsule. It is most convenient, however, to use an organic phase of a prepolymer concentration of from about 1% to about 70% on a weight basis, preferably from about 5% to about 50%.

The organic phase also contains the cross-linking agent of the present invention, which is present in an amount of from about 0.4 to about 7.5, preferably from about 0.7 to about 3, weight percent.

Once the organic phase has been formed, an emulsion is then prepared by dispersing the organic phase in an aqueous solution comprising water and a surface-active agent. The relative quantities of organic and aqueous phases are not critical to the practice of this invention, and can vary over a wide range, determined most by convenience and ease of handling. In practical usage, the organic phase will comprise a maximum of about 55% by volume of the total emulsion and will comprise discrete droplets of organic phase dispersed in the aqueous solution.

The surface active agent can be any of the wide variety of compounds known to be useful for lowering the surface tension of a fluid interface, including both nonionic and anionic surface active agents. The quantity of surface active agent is not critical but for convenience generally comprises from about 0.1% to about 5% by weight of the aqueous phase.

In some systems emulsion stability can be enhanced by adding a protective colloid to the aqueous phase. The protective colloid stabilizes a dispersed system against aggregation, flocculation and coalescense. Many materials are known to function as protective colloids and are available commercially. The colloid may be added to the aqueous phase prior to the formation of the emulsion or after the emulsion has been formed. Preferred protective colloids are lignin sulfonates or naphthalene-formaldehyde sulfonates. The exact quantity of the colloid is not critical; most conveniently between about 0.1% and about 5.0% colloid by weight in terms of the aqueous phase is utilized.

The droplet size of the emulsion is also not critical to the invention. For greatest utility, the droplet size will be in the range of from about 0.5 to about 4,000 microns in diameter, preferably from about 1 micron to about 100 microns in diameter, most preferably from about 1 to about 25 microns in diameter. The emulsion is prepared as is usual, employing any conventional high shear stirrer. Once the desired droplet size is obtained, mild agitation is generally sufficient to prevent proper growth throughout the balance of the process.

Once the desired droplet size has been attained, the overall system is then acidified to a pH of between about 0 and about 4.0, preferably between about 1.0 and about 3.0. This causes the prepolymer and cross-linker to polymerize by condensation in situ and form a shell completely enclosing each droplet. Acidification can be accomplished by any suitable means including any water-soluble acid such as formic, citric, hydrochloric, sulfuric, or phosphoric acid, and the like. Acidification can also be achieved by the use of acidic dispersants or surface-active agents, provided that they are added to the system after the emulsion has been formed.

As the polymer wall becomes more rigid, contact between the active groups on the prepolymer becomes more difficult. Thus, the in situ condensation polymerization reaction is self terminating and is generally allowed to run to completion. However, if desired, the reaction can be arrested before completion by raising the pH. In this manner, the wall tightness, rigidity and permeability can be controlled.

The rate of the in-situ condensation polymerization increases with both acidity and temperature depending on the pH. The reaction can therefore be conducted anywhere within the range or from about 20° C. to about 100° C., preferably between 40° C. and about 60° C. The reaction will generally be complete within a few hours, although with high acidity and high temperature it can be completed within minutes.

The resulting product is an aqueous suspension of the microcapsules in which the material in the organic phase is contained within the microcapsules. The aqueous phase of the suspension contains those adjuvants and other materials which were present in the aqueous phase of the emulsion.

The foregoing is a description of production of microcapsules according to the invention in which the capsules are produced from an oil-in-water emulsion and the encapsulated material comprises an organic liquid. This is the preferred type of product, and process, for the capsules of this invention. However, capsules of this invention may also be produced which contain an aqueous liquid, which may include pesticides and the like similarly dispersed, suspended or dissolved therein.

Such products may be produced using an encapsulation process in which microcapsules are produced from a water-in-oil emulsion and which the aqueous phase contains a non-etherified amino resin prepolymer and a water-soluble cross-linking agent of the type described herein. The emulsion is formed under conditions which do not favor reaction between the prepolymer and cross-linking agent; then conditions are changed so that they react and form a membrane around the water droplets. The resulting product is an oil suspension of such microcapsules.

The microcapsule suspensions thus produced may be utilized in the normal fashion of such products, i.e., by packaging the suspension and ultimately transferring the suspension into a spray tank or other spray equipment, in which it is mixed with water to form a sprayable suspension. Alternatively, the suspension of microcapsules may be converted into a dry microcapsule product by spray drying or other known techniques and the resulting material packaged in dry form.

To take advantage of the base-sensitivity of the microcapsules due to the presence of the cross-linking agent, for use the capsules are placed in a basic environment, directly or indirectly. Direct methods can be accomplished by adding a basic substance to the spray tank or spray equipment containing the microcapsules and water so that release of the encapsulated material can begin in the spray tank. In one convenient aspect of the invention, the microcapsules (either in suspension or dry form) are packaged with, but separately from, a suitable basic substance in any of a number of forms generally known as "twin packs" so that the basic substance is conveniently on hand, in an appropriate amount, for use in this way.

The basic substance may be any of a number of bases or basic substances and is utilized in an amount so as to provide a resulting pH in the presence of the base-sensitive microcapsules of from about 8 to about 13, preferably from about 9 to about 11. Preferred bases are alkali and alkaline earth metal hydroxides, hydroxides of quaternary ammonium salts such as ammonium and trialkyl ammonium hydroxides, and amines such as triethylamine.

Exposure of the capsules to a basic environment causes breakdown of the capsule wall by hydrolysis of the ester moieties introduced by use of the cross-linking agent. The rapidity of the breakdown may be varied depending on the choice of the identity and amount of cross-linking agent, the overall capsule wall content and construction, and the pH of the environment into which the capsule is put. Exposure of the capsules to that basic environment "triggers" degradation of the wall with a resulting change in the release profile of the capsule from that which would exist in an environment having a non-basic pH value. Depending on the above factors, the release rate may be changed dramatically, resulting in a relatively quick release of the encapsulated materials, or may be changed to a much lower extent, resulting in some, but not a dramatic, increase in release rate.

The base may be introduced so as to either directly or indirectly provide an environment in which the pH is from about 8 to about 13, preferably from about 9 to about 11 (in the presence of the capsules). In the direct method, the base is added in an amount so as to provide an environment within the aforesaid pH range at or close to the time of its addition, e.g. in the spray tank. However, after spraying such a product, the pH of the sprayed droplets will naturally increase due to an increased concentration of base as the water evaporates. Accordingly, in an indirect method the amount of base utilized in this invention may be less than that which will provide an immediate or near-immediate pH of the target value, but which is sufficient to provide such a pH after spraying as the sprayed water evaporates. For instance, establishment of a pH in the spray tank as low as about 7.5–9 would result in the pH of the environment (e.g., water droplet on plant surfaces) increasing to a value of from about 9 to about 11 as the water evaporates. Thus, the concept of this invention includes initially contacting the microcapsules with a basic substance in a spray tank or similar apparatus such that the initial environment is at a pH value of as low as about 7.5, then spraying or otherwise applying the resulting dispersion to foliage or other surfaces. In such an application the pH will increase as water evaporates to a preferred value of from about 9 to about 11.

Alternatively, the microcapsules may be sprayed without utilizing a base, in which case they would function as controlled release capsules, releasing the contained ingredient into the surrounding environment.

Biological effects of the encapsulated products can be enhanced by using a humectant such as polyethylene glycol or glycerol to improve hydrolysis of the ester moieties in the capsule walls when situated on foliar surfaces.

One of the advantages of the microcapsules of this invention is that they provide the possibility of producing a comparatively safer pesticidal product as compared to standard liquid or solid products but which still can provide quick release and thus ready availability of the encapsulated material for pest control.

For example, pyrethroid insecticides are known in some cases to provoke an adverse skin reaction. This reaction has been described as a burning, tingling, numbing or prickling sensation, which is most pronounced on regions of the handler's face. This reaction, known as paraesthesia, is generally associated with transfer of trace amounts of the pyrethroid to the handler's face through inadvertent touching by a contaminated hand. In current agricultural practices, compositions containing pyrethroids for application to plant foliage are provided in nonencapsulated forms, such as emulsifiable concentrates, wettable powders and dusts.

Microencapsulation of the pesticides utilizing the current invention may provide an increase in the safety of pesticide handling to the extent that the polymer wall of the microcapsule minimizes contact of the handler with the active pesticide. At the same time, the comparatively quick release properties which the compositions of this invention can be designed to possess enable the provision of the active ingredient into the environment in relatively the same concentration and with relatively the same effect as a typical nonencapsulated composition. This avoids typical drawbacks of slow release microcapsules which are not satisfactory when a relatively complete and quick release of the encapsulated ingredient is needed.

The invention may be used to produce capsule suspensions containing two materials which may be incompatible with each other, with one material being encapsulated and the other contained in the aqueous phase. Such combination products are storage-stable but produce a combination pesticidal product in the spray tank when a basic substance is added, so that both pesticides may be applied together.

The capsules of this invention have particular utility in control of insects which have an alkaline environment in their gut, particularly larvae of certain lepidoptera such as Heliothis spp. (i.e. Tobacco budworm), Helicoverpa spp. (i.e. Cotton bollworm), Spodoptera spp. (i.e. Beet, Fall, and Southern armyworms), *Agrotis ipsilon* (Black cutworm), *Pseudoplusia includens* (Soybean looper), *Trichoplusia ni* (Cabbage looper), *Bucculatrix thurberiella* (Cotton leafperforator), *Alabama argillacea* (Cotton leafworm), *Estigmene acraea* (Saltmarsh caterpillar), *Pectinophora gossypiella* (Pink bollworm), and *Ostrinia nubialis* (European cornborer). To be efficacious for this purpose, the capsules of this invention must include a cross-linking agent which on contact with a base at a pH of about 8–10 will cause complete or near complete release of the encapsulated insecticidal contents within four hours or less, the period of time in which the capsule is likely to remain within the insect's gut. Capsules of this type are sprayed or deposited without the accompanying basic substance, and function as controlled release microcapsules until consumed by the insect. These capsules are particularly useful in that they are not harmful to beneficial insects which do not have an alkaline environment gut or do not feed on plants. The insecticide chlorpyrifos has been found particularly useful for such purpose.

It has been found that release of the encapsulated ingredients via, basic hydrolysis of ester moieties in the capsule wall may be speeded up or enhanced by the use of a phase transfer catalyst such as a quaternary onium salt.

It should be noted that the ester moieties in the capsule walls may also be subject to hydrolysis in the presence of an acid environment, particularly an environment of pH about 1 to about 4. Thus triggering of release of the encapsulated ingredients may also be performed by placing these capsules in an environment of that nature.

The invention is further illustrated by the following examples:

EXAMPLE 1

Preparation of Cross-linkers

The following general procedure was used as an azeotrope method for preparing pentaerythritol derivatives of this invention. Note that the sensitivity of thiols to oxidative coupling requires that reactions at elevated temperatures are kept air free.

A solution of pentaerythritol, thioglycolic acid, glycolic acid and p-toluenesulfonic acid in toluene was purged with nitrogen. The solution was then azeotroped under a nitrogen blanket in a Dean and Stark distillation apparatus when a dense lower organic layer separated. The progress of the reaction was monitored by infra-red spectroscopy by the disappearance of the acid signal at ca 1700 $cm^{-1}$ and the appearance of ester signal at about 1735 $cm^{-1}$. The spectral data correlated with the amount of azeotroped water. When the desired conversion was complete the reactor was cooled to room temperature under nitrogen. Typical reaction times for an oil bath temperature of 155° C. were four hours.

In one illustration preparation the upper toluene layer was decanted and the solvent was evaporated to give a toluene soluble fraction (2%). The lower organic phase was dissolved in chloroform which was washed with water. The aqueous and chloroform phases were separated and each was evaporated to dryness to give respectively a chloroform soluble fraction (57%) and a water soluble fraction (41%).

Recipes for various materials prepared by the above process are given in Table I.

TABLE 1

Recipes and Summary Data for SH and/or OH Aliphatic Ester Derivatives

| | Alcohol | | | Acid | | | Ratio | Catalyst | | | Solvent | | Time | Yield | |
|---|---|---|---|---|---|---|---|---|---|---|---|---|---|---|---|
| Ex. | type | wt, g | mmol | type | wt, g | mmol | acid:alc | type | wt, mg | mmol | type | ml | (hr) | wt, g | % |
| | | | | | Mercapto-Acid Esters | | | | | | | | | | |
| 1A | P | 13.62 | 100 | MA | 38.69 | 420.0 | 4.20 | pTsOH | 78 | 0.40 | tol | 50 | 16 | 44.35 | 89 |
| 1B | DP | 6.36 | 25 | MA | 18.43 | 200 | 8.0 | pTsOH | 76 | 0.40 | tol | 75 | 48 | 16.62 | 82 |
| 1C | DP | 3.8 | 15 | 2MPA | 9.7 | 91.4 | 6.09 | pTsOH | 50 | 0.26 | xyl | 40 | | 12 | 95 |
| | | | | | Glycolate Esters. Acids | | | | | | | | | | |
| 1D | TMP | 4.47 | 33 | GA | 8.87 | 117 | 3.5 | pTsOH | 19 | 0.10 | tol | 50 | 13 | 9.62 | 94 |
| 1E | ME | 23.44 | 300 | GA | 22.82 | 300 | 1.0 | pTsOH | 57 | 0.3 | tol | 100 | 24 | 35.44 | 87 |
| 1F | 3MPD | 11.39 | 100 | GA | 15.36 | 200 | 2.0 | pTsOH | 38 | 0.20 | tol | 50 | 21 | 22.42 | 100 |
| | | | | | Mixed Glycolic Acid and Mercapto-Acid Esters | | | | | | | | | | |
| 1G | GLY | 5.32 | 20 | GA/MA seq | 6.08 | 66 | 3.3 | pTsOH | 43 | 0.22 | tol | 40 | 40 | 8.33 | 77 |
| 1H | P | 13.62 | 100 | GA/MA 1:1.1 | 35.48 | 440 | 4.4 | pTsOH | 76 | 0.4 | tol | 50 | 4 | 40.25 | 99 |
| 1J | P | 13.62 | 100 | GA/MA 1:3 | 41.26 | 400 | 4.0 | pTsOH | 76 | 0.40 | tol | 75 | 24 | 41.52 | 100 |
| 1K | P | 13.62 | 100 | GA/2MPA 1/1 | 38.71 | 420 | 4.2 | pTsOH | 27 | 0.14 | tol | 50 | 19 | 45.43 | 100 |
| 1L | DP | 6.36 | 25 | GA/MA 1:2 | 13.01 | 150 | 6.0 | pTsOH | 29 | 0.15 | tol | 50 | 48 | 16.67 | 100 |
| 1M | DP | 6.36 | 25 | GA/MA 1:1 | 12.61 | 150 | 6.0 | pTsOH | 29 | 0.15 | tol | 50 | 48 | 12.59 | 77 |
| | | | | | Mixed Lactic Acid or Lactide and Mercapto-Acid Esters | | | | | | | | | | |
| 1N | P | 13.62 | 100 | LA/MA 1:1 | 39.62 | 400 | 4.0 | pTsOH | 76 | 0.40 | tol | 50 | | | |
| 1O | P | 10.61 | 78 | Lt/2MPA 1:2 | | 288 | 3.7 | pTsOH | | | tol | 50 | 13 | 36.61 | |

TABLE 2

Mixed Glycolic Acid and Mercapto-Acid Esters - Solvent Free Preparations

| | Alcohol | | | Acids | | | pTsOH | | Time hr | | Total Yield | | Solvent Fraction (%) | | | |
|---|---|---|---|---|---|---|---|---|---|---|---|---|---|---|---|---|
| Ex. | type | wt, g | mmol | type | wt, g | mmol | mg | mmol | reflux | distln | wt, g | % | CHCl3 | water | toluene | insols |
| 1P | P | 13.62 | 100 | GA | 15.21 | 200 | 70 | 0.37 | 5 | 20 | 41.0 | 102 | 96 | 4 | — | — |
| | | | | MA | 20.26 | 200 | | | | | | | | | | |
| 1Q | P | 8.20 | — | MA | 3.00 | 32 | 10 | 0.05 | 4 | 4 vac | 9.0 | — | | | — | — |
| 1R | P | 20.43 | 150 | GA | 22.81 | 300 | 100 | 0.92 | 2 | 3 vac | 61.8 | 103 | 67 | 33 | — | — |
| | | | | MA | 30.26 | 330 | | | | | | | | | | |
| 1S | P | 13.62 | 100 | GA | 15.21 | 200 | 76 | 0.40 | 4 | 4 vac | 36.8 | 92 | 83.1 | 16.9 | — | — |
| | | | | MA | 20.27 | 220 | | | | | | | | | | |

TABLE 2-continued

Mixed Glycolic Acid and Mercapto-Acid Esters - Solvent Free Preparations

| | Alcohol | | | Acids | | | pTsOH | | Time hr | | Total Yield | | Solvent Fraction (%) | | |
|---|---|---|---|---|---|---|---|---|---|---|---|---|---|---|---|
| Ex. | type | wt, g | mmol | type | wt, g | mmol | mg | mmol | reflux | distln | wt, g | % | CHCl3 | water | toluene | insols |

Alcohols:
DP = Dipentaerythritol
GLY = Glycerol
3MPD = 3-mercaptopropanediol
3MPD = 3-mercaptopropanediol
MA = mercaptoacetic acid
2MPA = 2-mercaptopropionicacid
GA = glycolic acid
LA = lactic acid
P = pentaerythritol
TMP = trimethylolpropane
ME = mercaptoethanol
Lt = lactide (cyclic dimer of lactic acid)

Preparation of Cross-linkers by a Solvent Free Method

A mixture of pentaerythritol, glycolic acid, thioglycolic acid and para-toluenesulphonic acid as catalyst was stirred under a nitrogen purge for thirty minutes. The mixture was heated in an oil bath at 160° C. to reflux and under a nitrogen blanket for 2 hours to effect initial oligomerization. These conditions reduced the amount of monomeric thioglycolic (bp 96° C./5 mm Hg) and glycolic (mp 75–80° C.) acids and of pentaerythritol (bp 276° C./30 mm Hg) which might otherwise be lost in the subsequent distillation.

The reaction vessel was then cooled under nitrogen to about 100° C. and the reflux arrangement was reconfigured for distillation. Typically the mixture was then heated at about 100° C. under a water pump vacuum (ca 15 mm Hg) for 2 hours followed by high vacuum (ca I mm Hg) for 2 hours. Summary data for solvent free processes are collected in Table II The method afforded relatively high yields of poorly water soluble products.

EXAMPLES 2–17

Preparation of Microcapsules

A suspension of microcapsules containing as a pesticide either the insecticides chlorpyrifos or lambda-cyhalothrin or the herbicide butylate was prepared utilizing the Zeneca microencapsulation process wherein the pesticide was encapsulated within the polymeric shell wall formed by interfacial polymerization and condensation of a mixture of a butylated urea-formaldehyde prepolymer and a cross-linking agent containing sulfhydryl (—SH) and/or hydroxyl (—OH) groups.

The general procedure was as follows: the organic phase was comprised of the pesticide and, in some cases, dissolved in a solvent, a butylated urea-formaldehyde prepolymer and a cross-linking agent. The aqueous phase was comprised of a protective colloid, an emulsifier, and an acid dissolved in water. An emulsion is then prepared by dispersing the oil phase in the aqueous phase employing any conventional high shear stirrer until the desired particle size is achieved. The resulting oil in water emulsion is then heated to 50° C.±5° C. for three hours. The resulting capsule suspension was removed from the heat and post-formulated with suspending agents, ammonium hydroxide, and a biocide using a convention high shear stirrer.

A composition was prepared according to the foregoing procedure including ingredients as listed below:

EXAMPLE 2

| | Weight (g) |
|---|---|
| chlorpyrifos (technical grade) | 13.64 |
| Aromatic 200 solvent | 7.30 |
| Beetle 80 (etherified urea-formaldehyde resin available from Cytec) | 1.38 |
| PDGDM | 0.35 |
| Reax 85A (protective colloid) (20% solution) | 2.598 |
| Petro BAF (surfactant) | 0.018 |
| Sulfuric acid (50% solution) | 0.16 |
| Water | 14.921 |
| Xanthan gum (Kelzan product, available from Monsanto) | 0.030 |
| Attagel 40 (attapulfite clay, available from Engelhard) | 0.301 |
| Ammonium Hydroxide (30% solution) | 0.12 |
| Proxel GXL biocide (available from ICI) | 0.10 |
| Median Particle Size | 10.0µ |

EXAMPLES 3–4

Compositions were prepared according to the foregoing procedure including ingredients as listed below:

| | Weight (g) | |
|---|---|---|
| Example | 3 | 4 |
| chlorpyrifos (technical grade) | 17.78 | 17.78 |
| Aromatic 200 | 9.56 | 9.56 |
| Beetle 80 Resin | 3.86 | 4.34 |
| PDGDM | 1.00 | 0.48 |
| Reax 83A | 0.82 | 0.82 |
| Petro BAF | 0.027 | 0.027 |
| Sulfuric acid (50% solution) | 0.32 | 0.28 |
| Water | 26.25 | 26.25 |
| Kelzan | 0.060 | 0.060 |
| Attagel 40 | 0.60 | 0.60 |
| Ammonium Hydroxide (30% solution) | 0.14 | 0.13 |
| Proxel GXL | 0.10 | 0.10 |
| Median Particle Size | 8.9µ | 9.4µ |

EXAMPLES 5–6

Compositions were prepared according to the foregoing procedure including ingredients as listed below:

| Example | Weight (g) | |
|---|---|---|
| | 5 | 6 |
| chlorpyrifos technical | 17.71 | 17.78 |
| Aromatic 200 | 9.54 | 9.57 |
| Beetle 80 Resin | 3.84 | 3.86 |
| PDGDM | — | 0.53 |
| PTT | 0.95 | 0.53 |
| Reax 83A | 0.826 | 0.82 |
| Petro BAF | 0.028 | 0.027 |
| Sulfuric acid (50% solution) | 0.25 | 0.28 |
| Water | 26.11 | 26.25 |
| Kelzan | 0.062 | 0.06 |
| Attagel 40 | 0.600 | 0.60 |
| Ammonium Hydroxide (30% solution) | 0.12 | 0.13 |
| Proxel GXL | 0.10 | 0.10 |
| Median Particle Size | 9.2µ | 10.5µ |

EXAMPLES 7–8

Compositions were prepared according to the foregoing procedure including ingredients as listed below:

| Example | Weight (g) | |
|---|---|---|
| | 7 | 8 |
| Lambda-cyhalothrin (55% solution in Aromatic 200) | 14.25 | 15.09 |
| Beetle 80 Resin | 2.01 | 0.99 |
| PDGDM | 0.51 | 0.67 |
| Reax 85A (20% solution) | 3.633 | 3.604 |
| Petro BAF | 0.050 | 0.050 |
| Sulfuric Acid (50% solution) | 0.24 | 0.23 |
| Water | 20.020 | 20.045 |
| Kelzan | 0.030 | 0.031 |
| Attagel 40 | 0.301 | 0.302 |
| Proxel GXL | 0.11 | 0.11 |
| Sodium Hydroxide (25% solution) | 0.06 | 0.05 |
| Median Particle Size | 5.8µ | 5.9µ |

EXAMPLES 9–10

Compositions were prepared according to the foregoing procedure including ingredients as listed below:

| Example | Weight (g) | |
|---|---|---|
| | 9 | 10 |
| Lambda-cyhalothrin (55% solution in Aromatic 200) | 18.00 | 18.02 |
| Beetle 80 Resin | 1.16 | 1.21 |
| PTT | 0.29 | 0.81 |
| Reax 100M (40% solution) (protective colloid) | 1.478 | 1.504 |
| Petro BAF | 0.051 | 0.053 |
| Sulfuric Acid (50% solution) | 0.20 | 0.18 |
| Water | 18.128 | 18.217 |
| Kelzan | 0.031 | 0.032 |
| Attagel 40 | 0.307 | 0.303 |
| Proxel GXL | 0.11 | 0.11 |

-continued

| Example | Weight (g) | |
|---|---|---|
| | 9 | 10 |
| Sodium Hydroxide (25% solution) | 0.10 | 0.22 |
| Median Particle Size | 5.0µ | 5.2µ |

EXAMPLES 11–12

Compositions were prepared according to the foregoing procedure including ingredients as listed below:

| Example | Weight (g) | |
|---|---|---|
| | 11 | 12 |
| Butylate (technical grade) | 39.20 | 39.20 |
| Beetle 80 Resin | 2.10 | 2.08 |
| DPTA | 0.90 | — |
| DPMA | — | 0.90 |
| Reax 100M (40% solution) | 1.90 | 1.90 |
| Petro BAF | 0.081 | 0.080 |
| Sulfuric Acid (50% solution) | 0.26 | 0.23 |
| Water | 34.96 | 35.22 |
| Sodium Hydroxide (25% solution) | 0.16 | 0.16 |
| Median Particle Size | 12.0µ | 8.6µ |

EXAMPLES 13–14

Compositions were prepared according to the foregoing procedure including ingredients as listed below:

| Example | Weight (g) | |
|---|---|---|
| | 13 | 14 |
| Butylate (technical grade) | 15.52 | 15.51 |
| Beetle 80 Resin | 0.75 | 1.03 |
| PMGTM | 0.50 | — |
| DPDGTM | — | 0.26 |
| Reax 85A (20% solution) | 3.230 | 3.330 |
| Petro BAF | 0.053 | 0.052 |
| Sulfuric Acid (50% solution) | 0.21 | 0.21 |
| Water | 20.030 | 20.007 |
| Sodium Hydroxide (25% solution) | 0.13 | 0.14 |
| Median Particle Size | 5.6µ | 5.6µ |

EXAMPLES 15–17

Compositions were prepared according to the foregoing procedure including ingredients as listed below:

| Example | Weight (g) | | |
|---|---|---|---|
| | 15 | 16 | 17 |
| Butylate (technical grade) | 15.49 | 15.51 | 15.50 |
| Beetle 80 Resin | 1.02 | 1.00 | 1.00 |
| Q43 | 0.25 | — | — |
| PTT | — | 0.25 | — |
| PDGDM | — | — | 0.25 |
| Reax 85A (20% solution) | 3.364 | 3.256 | 3.339 |
| Petro BAF | 0.050 | 0.051 | 0.05 |
| Sulfuric Acid (50% solution) | 0.23 | 0.29 | 0.22 |
| Water | 20.409 | 20.199 | 20.269 |

-continued

| Example | Weight (g) | | |
|---|---|---|---|
| | 15 | 16 | 17 |
| Sodium Hydroxide (25% solution) | 0.10 | 0.16 | 0.20 |
| Median Particle Size | 6.4μ | 5.8μ | 11.0μ |

EXAMPLE 18

Biological Evaluation

The compositions of Examples 2–6 were tested for biological activity against two species, *Lygus hesperus* (a sucking insect) and *Heliothis virescens* (a foliar feeding lepidoptera with an alkaline gut).

Test 1

A. Contact/Residue Contact (Species: *Lygus hesperus*)

The test procedure was as follows:

*Lygus hesperius* was the subject in this test. Adult bugs in cages were sprayed at 250 l/h. There were four replicates of 10 insects for 5 rates of each formulation. Mortality assessments were made at 1, 2, 3, 4, 5, and 6 DAT.
The LC50s in ppm are given in Table 3:

TABLE 3

| Formulation | 1DAT | 2DAT | 3DAT | 4DAT | 5DAT | 6DAT |
|---|---|---|---|---|---|---|
| Chlorpyrifos technical | 313 | 310 | 311 | 313 | 313 | 325 |
| Example 2 | 760 | 544 | 424 | 367 | 327 | 294 |

B. Foliar Persistence (Species: *Heliothis virescens*)

The test procedure was as follows:

*Helicoverpa zea* was the subject of this test. Detached cotton leaves were sprayed at 250l/h. Neonate larvae were infested on disks of treated leaves. There were three replicates of 18 insects for 3 rates of each formulation. Mortality assessments were made at 1, 2, and 3 DAT.
The LC50s in ppm are given in Table 4:

TABLE 4

| Formulation | 1DAT | 2DAT | 3DAT | Total |
|---|---|---|---|---|
| Chlorpyrifos technical | 9.8 | 8.6 | 12.2 | 10.2 |
| Example 2 | 10.3 | 7.2 | 7.3 | 8.4 |

Test 2

A. Contact/Residue Contact (Species: *Lygus hesperus*)

Procedures were as follows:

Cardboard cages containing a fresh green bean were infested with 10 adult *Lygus hesperus* bugs. Four replicates per rate were sprayed at 250 liters/hectare. Materials were dissolved in 0.05% X-77 in water. Previous test results produced an LC50 of ~300 ppm for technical chlorpyrifos, so rates of 900, 600, 400, 267, and 178 ppm were chosen for Lorsban 4E. Results for CS formulations have frequently produced LC50s much higher at the start of the test, so rates of 2700, 1800. 1200, 800, 533 ppm were chosen for them. The Contact/Residue Contact procedure for *L. hesperus* was followed (as in Test 1 above), with mortality assessments made daily for four days.
The LC50s in ppm are as follows:

| Formulation | 1DAT | 2DAT | 3DAT | 4DAT |
|---|---|---|---|---|
| Lorsban EC | 239 | 220 | 214 | 205 |
| Example 3 | >2700 | 1203 | 909 | 679 |
| Example 4 | >2700 | 922 | 732 | 543 |
| Example 6 | >2700 | 2515 | 1846 | 1479 |
| UTC | 3% | 3% | 3% | 10% |

>2700 indicates ≦5% mortality at the highest rate
UTC—untreated control

B. Foliar Persistence (Species: *Heliothis virescens*)

Test procedures were as follows:

Cotton plants were sprayed at 250 liters/hectare. Previous tests produced LC50s of ~30 ppm and LC90s of ~90 ppm for Lorsban 4E against Heliothis, so rates of 100, 50, 25, and 12.5 ppm were chosen for all formulations. Plants were treated on three consecutive days, four rates per formulation, with the first two days' treatments kept in the glasshouse. On the third day, after the final treatment, treated leaves were detached for infestation. Three replicates of 15 insects per replicate were infested. Mortality assessments were made 2 days after infesting.
The LC50s in ppm are as follows:

| Formulation | 0DAT | 1DAT | 2DAT |
|---|---|---|---|
| Lorsban 4E | 74 | >>100 | >>100 |
| Example 3 | 146 | 102 | 46 |
| Example 4 | 203 | 58 | 70 |
| Example 5 | 167 | 498* | 149 |
| UTC | 2% | | |

*Data point anomaly due to lack of control at one rate

Test 3

A. Contact/Residue Contact (Species: *Lygus hesperus*)

The test procedure was as in Test 2.

The LC50s in ppm are as follows:

| Formulation | 1DAT | 2DAT | 3DAT | 4DAT | 5DAT | 6DAT |
|---|---|---|---|---|---|---|
| Lorsban 4E | 262 | 253 | 252 | 258 | 260 | 257 |
| Example 5 | — | 4558 | 2510 | 2134 | 1979 | 1939 |
| Example 6 | — | — | 1995 | 1839 | 1757 | 1711 |
| UTC | 5% | 5% | 5% | 10% | 15% | 18% |

— indicates no LC50 predicted due to insufficient data

B. Foliar Persistence (Species: *Heliothis virescens*)
The test procedure was as in Test 2.
The LC50s in ppm are as follows:

| Formulation | 0DAT | 2DAT |
|---|---|---|
| Lorsban 4E | 104 | — |
| Example 5 | 164 | 177 |
| Example 6 | 81 | 81 |
| UTC | 2% | 2% |

— indicates no LC50 predicted due to insufficient data

What is claimed is:

1. A microcapsule formed of an aminoplast shell wall and an encapsulated ingredient or ingredients enclosed within the wall, the wall having been produced by a microencapsulation process comprising reacting an etherified amino resin prepolymer with a cross-linking agent wherein said cross-linking agent is the ester or thioester reaction product of (a) a multifunctional alcohol selected from the group consisting of pentaerythritol, dipentaerythritol, tripentaerythritol, trimethylolpropane, glycerol, 3-mercaptopropane-diol, 1,2,4-butanetriol, 1,3,5-cyclohexanetriol, 1,2,3-heptanetriol and sorbitol, and (b) one or more 2-(hydroxy) and/or 2-(thiol) $C_2$–$C_6$ alkanoic acids, wherein the resulting ester and/or thioester groups are capable of being cleaved under basic conditions.

2. A method of controlling a pest comprising applying to the pest, to the locus of the pest, or to a location in which the pest may be present, a composition comprising a microcapsule according to claim 1 in which the encapsulated ingredient comprises a pesticide, said composition being applied in a pesticidally effective amount.

3. A microcapsule according to claim 1 in which the multifunctional alcohol is pentaerytbritol and the cross-linking agent has the formula

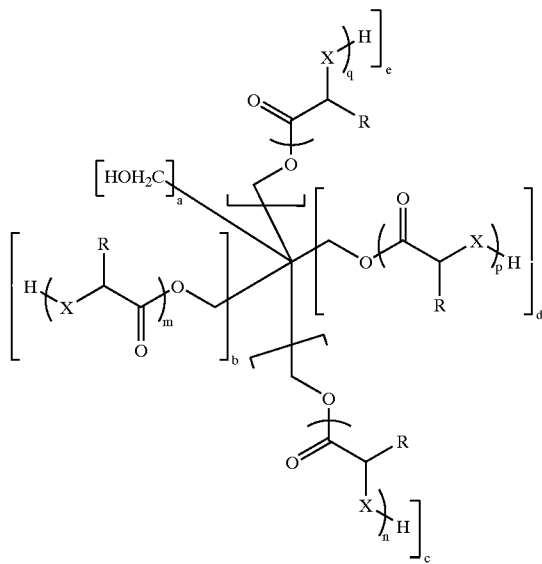

(IIa)

where R is —H or $C_1$–$C_4$ alkyl groups which may alternate randomly; X is oxygen or sulfur which may alternate randomly; $a \leq 2$; and b, c, d, e are zero or a number from 1 to 4, where $a+b+c+d+e=4$; and m, n, p, and q are independent values from 1 to 20 or

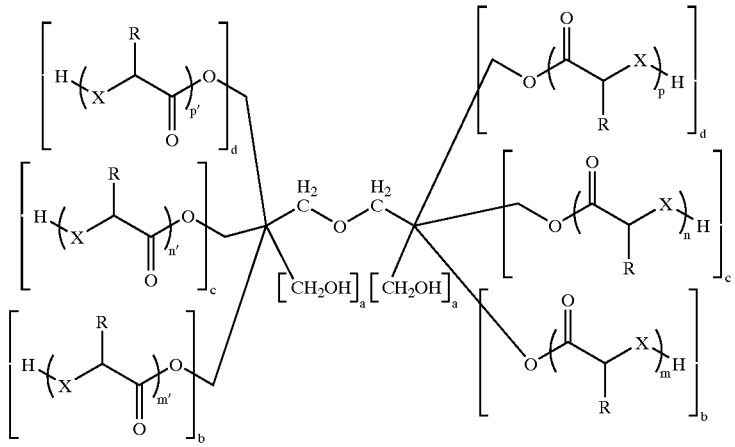

where R is —H or $C_1$–$C_4$ alkyl groups which may alternate randomly; X is oxygen or sulfur which may alternate randomly; a, a'$\leq 2$ and b, b', c, c', d, and d' are zero or a number from 1 to 3 where $a+b+c+d+a'+b'+c'+d'=6$; and m, 4. A microcapsule according to claim 3 in which the cross-linking agent has the formula

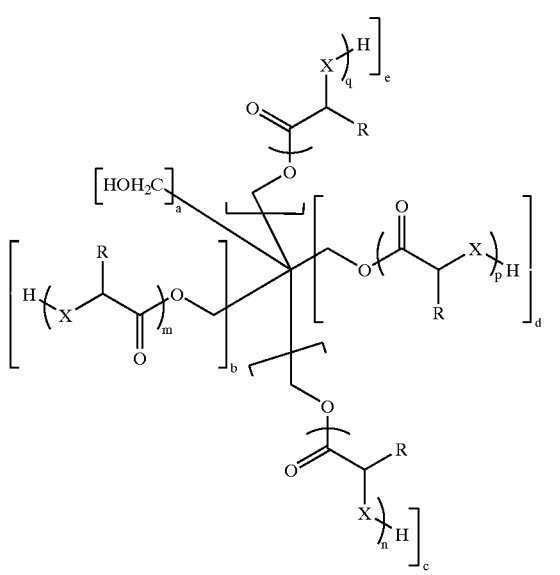

(IIa)

and a is zero.

5. A microcapsule according to claim 4 in which R is hydrogen.

6. A method according to claim 2 in which the pest is selected from undesirable vegetation, insects, acarids, mites and rodents.

7. A method according to claim 2 in which the microcapsules are placed in a basic environment such that cause cleavage of the ester moiety occurs, resulting in breakdown of the capsule walls.

8. A microcapsule according to claim 3 in which the alkanoic acid is selected from glycolicacid, mercaptoacetic acid, lactic acid, thiolactic acid, and the cyclic dimer of lactic acid.

9. A microcapsule according to claim 3 in which the cross-linking agent has the formula (IIa) and is prepared by reaction of pentaerythritol with glycolic and mercaptoacetic acids in a molar ratio of 1:2:2 respectively.

10. A microcapsule according to claim 3 in which the cross-linking agent has the formula (IIa) and is prepared by reaction of pentaerythritol with mercaptoacetic acid in a molar ratio of 1:4.

11. A microcapsule according to claim 3 in which the cross-linking agent has the formula (IIa) and is prepared by reaction of pentaerythritol with glycolic and mercaptoacetic acids in a molar ratio of 1:1:3 respectively.

12. A microcapsule according to claim 3 in which the cross-linking agent has the formula (IIb) and is prepared by reaction of dipentaerythritol with thiolactic acid in a molar ratio of 1:6.

13. A microcapsule according to claim 1 in which the wall is produced by a microencapsulation process comprising in situ condensation of an amino resin prepolymer and in which the prepolymer is reacted with the cross-linking agent.

14. A microcapsule according to claim 13 in which the amino resin prepolymer is a urea-formaldehyde or a melamine-formaldehyde prepolymer.

15. A microcapsule according to claim 14 in which the prepolymer is an etherified urea-formaldehyde or melamine-formaldehyde prepolymer.

16. A microcapsule according to claim 1 which is stable under neutral or mildly acidic conditions.

17. A microcapsule according to claim 1 in which the encapsulated material comprises one or more agricultural chemicals.

18. A microcapsule according to claim 1 in which the encapsulated material comprises one or more agricultural or non-agricultural pesticides.

19. A microcapsule according to claim 18 in which the encapsulated material comprises one or more insecticides.

20. A microcapsule according to claim 19 in which the encapsulated material comprises one or more pyrethroid insecticides.

21. A microcapsule according to claim 19 in which the encapsulated material comprises lambda-cyhalothrin.

22. A microcapsule according to claim 19 in which the encapsulated material comprises one or more insecticides effective as stomach poisons.

23. A method according to claim 2 in which the composition also comprises a basic substance sufficient to cause cleavage of the ester moiety.

24. A method according to claim 2 comprising applying to a locus at which insects feed, a microcapsule according to claim 1 containing an insecticide which is a stomach poison, the cross-linking agent being selected so as to produce relatively rapid disintegration or degradation of the microcapsule wall when in contact with an alkaline environment in an insect's gut.

25. A microcapsule according to claim 1 in which the ester moiety comprises from about 5 to about 80 percent by weight of the shell wall.

26. A microcapsule according to claim 1 in which the shell wall comprises from about 1 to about 70 percent by weight of the microcapsule.

27. A microcapsule according to claim 1 in which the shell wall comprises from about 5 to about 50 percent by weight of the microcapsule.

28. A microcapsule according to claim 1 having an average diameter of from about 1 to about 100 microns.

29. An aqueous suspension of microcapsules wherein the microcapsules are as defined in claim 1.

30. An aqueous suspension of microcapsules according to claim 29 wherein the aqueous phase further comprises a phase transfer catalyst.

31. An aqueous suspension of microcapsules according to claim 29 in which a pesticide is contained in the microcapsules and/or in the aqueous phase.

32. An aqueous suspension of microcapsules according to claim 29 wherein the encapsulated ingredient comprises a pesticide and the aqueous phase contains a second pesticide.

33. An aqueous suspension of microcapsules according to claim 32 in which the encapsulated pesticide is substantially incompatible with the second pesticide.

34. A composition comprising a microcapsule according to claim 1 and a basic substance.

35. A composition according to claim 34 in which the basic substance is selected from alkali and alkaline earth metal hydroxides, ammonium hydroxide, quaternary ammonium hydroxides, and amines.

36. A method according to claim 24 in which the hydrolyzable ester moiety is selected so as to produce disintegration or degradation of the microcapsule wall within approximately four hours or less.

* * * * *

UNITED STATES PATENT AND TRADEMARK OFFICE
CERTIFICATE OF CORRECTION

PATENT NO.      : 6,544,540 B2
DATED           : April 8, 2003
INVENTOR(S)     : Van Koppenhagen et al.

It is certified that error appears in the above-identified patent and that said Letters Patent is hereby corrected as shown below:

Column 21,
Line 34, replace "pentaerytbritol" with -- pentaerythritol --.

Column 22,
Line 61, insert -- m', n, n', p and p' are independent values from 1-20 --.
In the drawing that follows line 34, on the left-hand side of the drawing starting with the top group enclosed by square brackets and working down to the bottom group enclosed by square brackets, replace "$_d$" with -- $_{d'}$ --, "$_c$" with -- $_{c'}$ -- and "$_b$" with -- $_{b'}$ --, respectively; and at the center of the drawing, replace the first occurrence of "$[CH_2OH]_a$" with -- $[CH_2OH]_{a'}$ --.

Column 23,
Line 39, replace "glycolicacid" with -- glycolic acid --.

Signed and Sealed this

Fourteenth Day of October, 2003

JAMES E. ROGAN
*Director of the United States Patent and Trademark Office*